United States Patent [19]
Sartorius et al.

[11] 3,951,755
[45] Apr. 20, 1976

[54] PROCESS FOR PREPARING TECHNICALLY PURE ACETIC ACID BY EXTRACTIVE DISTILLATION

[75] Inventors: Rudolf Sartorius; Hans Stapf, both of Frankfurt am Main, Germany

[73] Assignee: Hoechst Aktiengesellschaft, Frankfurt am Main, Germany

[22] Filed: Feb. 18, 1975

[21] Appl. No.: 550,643

[30] Foreign Application Priority Data
Feb. 20, 1974 Germany............................ 2408011

[52] U.S. Cl..................................... 203/16; 203/53; 203/60; 260/541
[51] Int. Cl.² ..................... B01D 3/40; C07C 51/44; C07C 53/08

[58] Field of Search.......................... 203/16, 53, 60; 260/541

[56] References Cited
UNITED STATES PATENTS

| | | | |
|---|---|---|---|
| 2,425,542 | 8/1947 | Krieble | 260/541 |
| 2,578,698 | 12/1951 | Hanford | 260/541 |
| 3,890,208 | 6/1975 | Henneberg | 203/58 |

Primary Examiner—Wilbur L. Bascomb, Jr.
Attorney, Agent, or Firm—Henry W. Koster

[57] ABSTRACT

Process for preparing technically pure acetic acid from water - acetic acid mixtures by extractive distillation with N-methyl acetamide.

5 Claims, 1 Drawing Figure

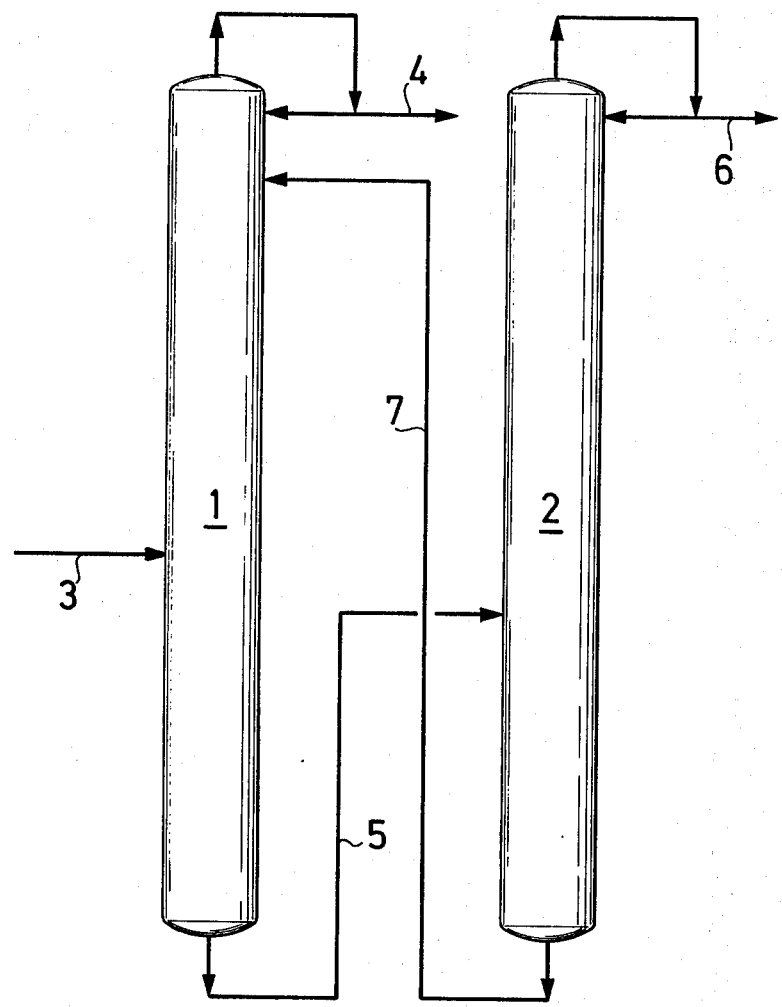

PROCESS FOR PREPARING TECHNICALLY PURE ACETIC ACID BY EXTRACTIVE DISTILLATION

The concentration of water-containing acetic acid is effected technically either by extraction or by entrainer distillation. In some cases the concentration is also effected without any entrainer only by distillation, especially when the starting product has a relatively high acetic acid content.

Processes have already been described, wherein the concentration is carried out by extractive distillation, for example, with high boiling solvents prepared from products of the carbonization of wood, derivatives of ethylene glycol or dimethyl aniline as extracting agents. These processes have not become industrially important hitherto, owing to the fact that the extracting agents used did not show a completely satisfactory efficiency or had further disadvantages. Dimethyl aniline, for example, forms an azeotrope with water, the working up whereof requires an additional expenditure. Furthermore, it has not been disclosed whether technically pure acetic acid may be obtained in one processing step in said process and, if it is possible, in which way.

Recently it has become known from German Offenlegungsschrift No. 2.201.827 that mixtures of acetic acid and water may be fractionated into water and technically pure acetic acid by extractive distillation with dimorpholyl ethane. This process however presents a series of disadvantages caused by the unfavorable melting and boiling point of 72° and 204.8°C respectively.

The conduits and pumps for the circulating product must be intensely heated owing to the relatively high melting point. Especial difficulties may arise when interrupting operating, since the columns may be obstructed in this case. The high melting point requires operating in vacuo of both columns necessary for carrying out the process, on the one hand to avoid thermal decompositions and on the other hand to enable heating of the column with the technically usual steam of from 15 to 20 atmospheres gauge.

The invention was concerned with the problem to find a process fully profiting from the advantages of the extractive distillation but not showing the disadvantages of the extracting agents used hitherto (low efficiency, forming of azeotropes, unfavorable melting and boiling point). Moreover it should be possible to use within limits as flexible as possible on mixtures of varying contents of acetic acid.

It has been found that N-methyl acetamide is especially suitable for this purpose.

The present invention consequently provides a process for preparing technically pure acetic acid from mixtures of water and acetic acid by extractive distillation, which comprises submitting the water-containing acetic acid to an extractive distillation with N-methyl acetamide in a first step and separating the acetic acid from N-methyl acetamide by rectification in a second step.

N-methyl acetamide has an excellent extractive effect for acetic acid, does not form azeotropes, and is chemically and thermally stable under the reaction conditions. Its melting and boiling point are substantially more favorable than those of dimorpholyl ethane. A consequence thereof is that the first of the two columns required may be operated at atmospheric pressure and that the technically usual steam of a pressure of 15 atmospheres gauge is sufficient.

When using as coefficient for the extractive effect the weight ratio of extracting agent/acetic acid required for decomposing the following values are obtained opposing dimorpholyl ethane to N-methyl acetamide:

| | dimorpholyl ethane | N-methyl acetamide |
|---|---|---|
| melting point | 72°C | 28 – 29°C |
| boiling point$_{760\ mm\ Hg}$ | | 206°C |
| boiling point$_{100\ mm\ Hg}$ | 204.8°C | 142°C |
| ratio extracting agent/acetic acid | 1.7 – 1.9 | 1.22 – 1.23 |

Two continuously operating columns are required for carrying out the process according to the invention.

The invention will be described by way of example in the accompanying drawing which is a flow scheme of the process according to the invention:

The first column (1) and 45 bubble-cap plates and operated at atmospheric pressure. The N-methyl acetamide was fed to the column via conduit (7) at the 40$^{th}$ plate (counted from the bottom) and the mixture to be fractionated at the 20$^{th}$ plate via conduit (3). Water practically free from acetic acid was obtained at the top of the column (1). A part was used as reflux, the other part was drawn off via conduit (4). An anhydrous mixture of acetic acid and N-methyl acetamide was obtained in the sump of the column (1). Said mixtures was passed to the column (2) thereafter connected via conduit (5) where it was fractionated in vacuo into a technically pure acetic acid and N-methyl acetamide. Column (2) was a filled column having about 40 theoretical plates. The mixture was fed to the column at a level corresponding approximately to the 15$^{th}$ plate (counted from the bottom). Technically pure acetic acid was obtained as the top product which was then drawn off via conduit (6), excluding the reflux. In the sump of the column (2) N-methyl acetamide practically free from acetic acid was obtained, which was recycled to the column (1) via conduit (7) as extracting agent-optionally with the addition of small amounts of water.

The acetic acid obtained as the top product of the column (2) met all the requirements made for "technically pure acetic acid". The degree of purity of the acid varied from about 99.8 to 99.9%, the melting point was from 16.4° to 16.45°C, the resistancy to permangante was more than 3 hours.

The N-methyl acetamide was chemically and thermally stable under the reaction conditions and may be recycled consequently. An additional energy saving may be obtained by a suitable heat exchange, for example, of the bottom product of column (2) for the feed stock of column (1).

The melting point of the N-methyl acetamide of from 28° to 29°C may be reduced to about 15°C by adding small amounts of water of up to 5 %, without affecting the extractive effect.

The process according to the invention may be used within wide concentration limits of the acetic acid, espcially at concentrations of from 35 to 75% of acetic acid in the acetic acid-water mixture susceptible of being fractionated.

From 120 to 140 kg of N-methyl acetamide were added preferably for 100 kg of pure acetic acid. The following examples illustrate the invention.

EXAMPLE 1

A mixture of 45.5% by weight of acetic acid and 54.5% by weight of water, previously heated to 90°C was fed to a rectification column (1) having 45 plates alltogether and operating at atmospheric pressure at the 20$^{th}$ plate (counted from below).

A mixture of 95% by weight of N-methyl acetamide and 5% by weight of water preheated to 90°C was simultaneously introduced into the column at the 40 plate (counted from below), the quantity of said mixture being calculated such that 59 parts by weight of N-methyl acetamide-water mixture were used for 100 parts by weight of acetic acid-water mixture, corresponding to a weight ratio of N-methyl acetamide and acetic acid of 1.23:1.

Water practically free from acetic acid (acetic acid contend of maximally 0.01%) was obtained as the head product, the head temperature being 100°C and the reflux ratio 0.33. The sump temperature was 166°C and an anhydrous mixture of acetic acid and N-methyl acetamide was obtained in the sump.

The bottom product was continuously drawn off over a levelling bulb, cooled to approximately 90°C and conducted to a series-connected column (2). Said column was charged with filling bodies, the package corresponding to approximately 40 theoretical plates. It was operated in vacuo at 100 torrs, measured at the top of the column. The bottom product drawn off from the column (1) was fed to the column at a level approximately corresponding to the 15$^{th}$ plate.

Technically pure acetic acid was obtained as the head product, the head temperature being 61°C and the reflux ratio of from 2 to 3. The acetic acid obtained had a degree of purity of 99.8%, the melting point was 16.4°C and the resistancy to permanganate was greater than 3 hours.

The sump temperature in column (2) was 146°C. The N-methyl acetamide obtained in the sump was drawn off continuously, cooled and recycled to column (1) after having added small quantities of water corresponding to 5% of water in the mixture.

EXAMPLE 2

The apparatus and the method used were the same as in example 1. Anhydrous N-methyl acetamide was however used instead of the mixture of 95% by weight of N-methyl acetamide and 5% by weight of water, i.e. 56 parts of anhydrous N-methyl acetamide were used for 100 parts of acetic acid-water mixture. This corresponded to a weight ratio of N-methyl acetamide to acetic acid of 1.23:1. Water practically free from acetic acid was obtained as head product as in example 1 and acetic acid of the same quality as in example 1 was obtained as the head product of column (2). The sump product of column (2)-N-methyl acetamide-was recycled to column (1).

EXAMPLE 3

The apparatus and the method used corresponded to that of Example 1. The mixture susceptible of being fractionated consisted of 64.7% by weight of acetic acid and 35.3% of water. A mixture of 97.5% of N-methyl acetamide and 2.5% by weight of water was used as extracting agent. Its quantity was calculated such that 80.7 parts of 97.5% N-methyl acetamide were used for 100 parts of acetic acid. This corresponded to a weight ratio of N-methyl acetamide/acetic acid of 1.22:1.

The head product of column (1) was water practically free from acetic acid as in example 1 and the head product of column (2) was technically pure acetic acid having a degree of purity of 99.9% of acetic acid, a melting point of 16.45°C and a resistancy to permanganate of more than 3 hours.

The bottom product of column (2)-N-methyl acetamide-was recycled to column (1) after cooling and adding small quantities of water corresponding to 2.5% by weight of water in the mixture.

What is claimed is:

1. Process for preparing technically pure acetic acid from mixtures of water and acetic acid by extractive distillation, which comprises submitting the water-containing acetic acid to an extractive distillation with N-methyl acetamide in a first step and fractionating the acetic acid from N-methyl acetamide in a second step by rectification.

2. Process as claimed in claim 1, which comprises using from 120 to 140 kg of N-methyl acetamide for 100 kg of pure acetic acid.

3. Process as claimed in claim 1, which comprises adding to the N-methyl acetamide up to 5% of water in order to reduce its melting point.

4. Process as claimed in claim 1, which comprises operating under a pressure of from 0.1 to 0.2 atmosphere gauge at the head of the column in the second step.

5. Process as claimed in claim 1, which comprises recycling the N-methyl acetamide recovered in the second step to the first step without intermediate purification.

* * * * *